United States Patent [19]

Fiedler et al.

[11] Patent Number: 5,331,973
[45] Date of Patent: Jul. 26, 1994

[54] METHOD FOR OBTAINING STOOL SAMPLES FOR GASTROINTESTINAL CANCER TESTING

[76] Inventors: Paul N. Fiedler, 200 Hemlock Rd., New Haven, Conn. 06515; Robert A. Levine, 31 Pilgrim La., Guilford, Conn. 06437; Stephen C. Wardlaw, 128 Sunset Hill Dr., Branford, Conn. 06405

[21] Appl. No.: 31,533

[22] Filed: Mar. 15, 1993

[51] Int. Cl.⁵ .............................................. A61B 5/00
[52] U.S. Cl. ................................... 128/760; 128/638
[58] Field of Search ......... 128/638, 749, 759; 422/56, 57, 58, 61; 435/28, 805, 7.92; 436/66

[56] References Cited

U.S. PATENT DOCUMENTS

| | | |
|---|---|---|
| 3,718,431 | 2/1973 | Wild . |
| 3,996,006 | 12/1976 | Pagano . |
| 4,175,923 | 11/1979 | Friend . |
| 4,259,964 | 4/1981 | Levine . |
| 4,273,741 | 6/1981 | Levine . |
| 4,365,970 | 12/1982 | Lawrence et al. ............ 422/58 |
| 4,367,750 | 1/1983 | Levine . |
| 4,420,353 | 12/1983 | Levine . |
| 4,559,949 | 12/1985 | Levine . |
| 4,615,982 | 10/1986 | Lawrence . |
| 4,645,743 | 2/1987 | Baker et al. . |
| 4,789,629 | 12/1988 | Baker et al. . |
| 4,804,518 | 2/1989 | Levine et al. . |
| 4,808,379 | 2/1989 | Wardlaw et al. . |
| 4,849,173 | 7/1989 | Chang . |
| 4,956,300 | 9/1990 | Wells . |
| 5,064,766 | 11/1991 | Wardlaw et al. . |
| 5,094,956 | 3/1992 | Grow et al. . |

OTHER PUBLICATIONS

"Cytologic Detection of Colorectal Cancer After...", by Gordon et al., pp. 106-110, Jul. 1, 1991.
"A Method of Obtaining, Processing, and Analyzing...", by Gaspari et al., *Journal of Immun. Methods*, pp. 85-91, 1988.
"Gut Lavage Fluid Proteins as Markers...", by S. O'Mahony et al., pp. 940-944, 1991.
"Haemoglobin in Gut Lavage Fluid as a Measure of Gastrointestinal Blood Loss," *The Lancet*, vol. 340, pp. 1381-1382, Dec. 5, 1992.

*Primary Examiner*—Lee S. Cohen
*Assistant Examiner*—Brian M. Green
*Attorney, Agent, or Firm*—Price, Heneveld, Cooper, DeWitt & Litton

[57] ABSTRACT

The specification discloses a method for enhancing the reliability of screening tests used for detecting the presence or absence of chemical markers associated with gastrointestinal cancer. The method comprises the steps of providing a laxative purge for administration to a patient, collecting a watery fecal sample and then applying the watery fecal sample to a test medium having an indicator to indicate the presence of chemical markers associated with gastrointestinal cancer, if there. Two alternative methods are suggested for obtaining a watery fecal sample. In a first embodiment, the purge is administered to the patient following a recent bowel movement and the first watery post-purge bowel movement is collected. In a second embodiment, the purge is administered to the patient, the first post-purge bowel movement is discarded and the second watery post-purge bowel movement is collected.

16 Claims, 1 Drawing Sheet

HOURS 0    1    2    5    8    22

LS-H

LS-B

METHOD FOR OBTAINING STOOL SAMPLES FOR GASTROINTESTINAL CANCER TESTING

BACKGROUND OF THE INVENTION

The present invention relates to a method for enhancing the collection of stool samples which are used for the detection of gastrointestinal cancer.

Common screening tests for gastrointestinal cancers involve obtaining a sample of stool and exposing the sample to one or more reagents specially selected to react with a targeted chemical marker associated with gastrointestinal cancer suspected of being in the sample. If the targeted chemical marker is indeed present in the stool sample, a recognizable result is produced by the screening test. Among the many available chemical markers which are the targets of presently used stool screening tests are hemoglobin and other blood-related proteins, collectively referred to as fecal occult blood (FOB).

Stool is formed in the large intestine. Chyme, the digested but unabsorbed food residue, passes from the small intestine into the large intestine where most of the water present in the thyme is absorbed, usually leaving a small amount of fluid to be excreted in the usually semi-solid stool. Most of the water absorption in the large intestine occurs in the proximal half of the colon, known as the absorbing colon, while the distal colon, also known as the storage colon, functions primarily for storage prior to excretion.

Stool residing in the storage colon, and upon excretion, is normally about three-fourths water and one-fourth solid matter. The solid matter is composed of bacteria, fat, inorganic matter, enzymes and other proteins, and undigested roughage of food among other components. During times of constipation, the level of water in stool is even less because of the longer residence time of the stool in the absorbing colon.

There are a number of techniques commonly used today in the collection of stool samples. The most common technique involves using a small paddle to fish a sample of excreted stool out of the toilet bowl. The sample is then wipe on a test card for further processing. U.S. Pat. No. 3,996,006 to Pagano discloses a device known as HEMOCCULT which utilizes such a technique to test for occult gastrointestinal bleeding by testing for FOB.

Another technique for collecting stool samples involves directly wiping the anal area following defecation with a pliant test wipe known as HEMAWIPE. A number of prior patents disclose the use of such a technique including U.S. Pat. Nos. 4,808,379, 4,804,518, 4,559,949, 4,420,353, 4,367,750, 4,273,741, and 4,259,964. HEMAWIPE also tests for occult gastrointestinal bleeding by testing for FOB.

In other tests, the patient is asked to defecate directly into the collection container. In some tests, the stool sample is tested as collected. In other tests, the stool is liquified prior to testing.

In all of these tests, the stool sample collected is defecated in the normal course of a patient's normal bowel routine. Even so, it is widely recognized that most existing tests for chemical markers such as FOB are subject to a substantial number of false negatives and false positives. The resulting errors can severely hamper diagnoses and are potentially deleterious to the patient's well being.

SUMMARY OF THE INVENTION

The present invention comprises the steps of administering a laxative purge to a patient, collecting a watery stool sample and then subjecting the collected stool sample to a diagnostic assay which tests for the presence of chemical markers associated with gastrointestinal cancer.

Generally, the first post-purge watery stool sample collected is satisfactory for the diagnostic assay, although the second post-purge watery stool sample may be preferred. Surprisingly, the present invention allows the doctor to determine with a higher level of confidence whether the diagnostic assay is "truly" positive or negative. This confidence in the assay results allows the doctor to make a more accurate diagnosis of the patient's condition. Armed with this information, the doctor can select an appropriate course of treatment. Follow-up tests can then be used to determine whether the treatment has been successful and, if not, further tests can then be conducted.

Without being bound to any particular theory, it is believed that the present invention yields a better stool sample for testing purposes because the chemical markers associated with gastrointestinal cancer in stool samples can become changed by the enzymes and bacteria present in stool if they remain in contact with the stool during its formation in the large bowel. This change in character of the chemical markers present in stool samples presents a far more significant impediment to obtaining accurate test results than heretofore appreciated. Obviously, the consequences of "false negative" test results can be quite severe, as in the case of a hidden colonic malignancy. Conversely, if there are a large number of "false positive" tests, the expense and possible complications of additional follow-up tests involved are also considerable. The present invention obviates or moderates the potential interference of enzymatic or bacterial degradation of chemical markers associated with gastrointestinal cancer in stool samples.

DESCRIPTION OF THE PREFERRED EMBODIMENT

Figure 1:
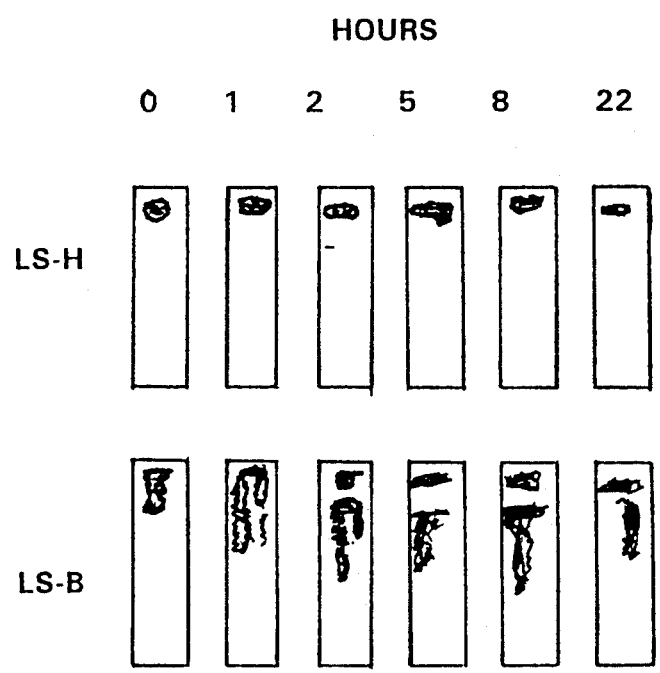
FIG. 1 shows developed chromatography strips comparing the migratory properties of whole blood vs. hematin in purged (liquid) stool samples with the passage of time.

In the preferred embodiment, a laxative purge is ingested and the first watery stool is collected. Solid stool present in the rectum and sigmoid colon at the time the purge is initiated is evacuated soon after the laxative is administered. This material is discarded unless a baseline value is sought. The first watery stool passed usually contains at least some fecal material that has been rapidly transported through the colon. While this sample may be suitable for some assays, in most situations stools collected later during the purge will be of greater diagnostic utility.

Additionally, two alternative embodiments are disclosed. In the first, the laxative purge is administered immediately after a bowel movement and the first and subsequent watery post-purge bowel movement are collected in separate containers. In the second embodiment, the purge is administered to the patient, any solid stool and the first watery post-purge bowel movement are discarded and the second and subsequent watery post-purge bowel movement are collected in separate containers. Each of these embodiments provides the opportunity to obtain stool samples having a higher yield of FOB because the collected stool has a shorter residency time in the colon.

Ideally, the laxative purges are administered to the patient orally. Among the laxative purges which can be used in the preferred embodiment are phosphosoda or magnesium titrate. Preferred laxative purges not only reduce the residence time of a patient's stool in the large bowel, they also do not affect the FOB present in the stool in order to facilitate proper diagnostic testing. In addition, preferred laxative purges maintain the chemical and biologic integrity of stool samples to allow the stool to be stored for a period of time after collection prior to testing. A particularly preferred laxative purge is a phosphosoda purge available from Fleets Inc., Lynchburg, Va. Use of these laxatives also diminishes hemorrhoidal bleeding, a source of false positive results in occult colon cancer screening.

To obtain a proper liquid stool sample, the patient must ingest sufficient laxative purge. Generally, sufficient liquid stool is obtained by following the manufacturer's instructions. It is within the ability of one of ordinary skill in the art to determine the proper dosage of the purge if variation is required.

If after the ingestion of the purge, the first post-purge bowel movement is solid, the first post-purge bowel movement is discarded and the first watery stool is collected. If the second bowel movement remains solid, a second laxative purge can be administered to the patient and the first watery bowel movement excreted by the patient is collected. Following collection, the fecal sample is then subjected to diagnostic testing.

If testing is not going to be immediate, liquid stool samples obtained by laxative purge may be stable for about one to two days at room temperature and about, five days if refrigerated following collection. Addition of a preservative such as ethylenediamine-tetraacetic acid (EDTA) can enhance the stability of the sample even more.

The present method of obtaining a watery stool sample is ideal for the recovery of chemical markers indicative of gastrointestinal disease that are easily degraded or otherwise altered by the harsh conditions present in solid stool. Hemoglobin, a protein, is but one chemical marker associated with gastrointestinal malignancy. Gastrointestinal cancers may produce other chemical markers, such as RAS DNA oncogenes and carcinoembryonic antigen (CEA), a protein. Both CEA and RAS are like hemoglobin in that they are subject to chemical breakdown by action of the enzymes and bacteria present in solid stool.

EXAMPLE

The following example is directed to a preferred embodiment of the present invention and is not to be construed as limiting the scope of the invention.

In the discussion below, the chromatographic stool assay system for the determination of the source of occult gastrointestinal bleeding disclosed in U.S. Pat. No. 5,064,766 to Wardlaw et al. is used to demonstrate the advantages of using a watery stool in a FOB diagnostic test. The Wardlaw et al. assay system distinguishes native hemoglobin (or whole blood) from hematin by exploiting electrical charge differences between these compounds. Gastric acid present in the stomach breaks down uncharged hemoglobin from upper GI bleeding to hematin and related hemoglobin breakdown products, which are highly charged. The charged hematin tends to "stick" to the chromatographic test paper, while the uncharged hemoglobin from the lower GI tends to migrate with the solvent. This provides a means for identifying whether the "blood" identified on the chromatographic paper originated in the upper or lower GI.

A disadvantage of this assay, however, is that it sometimes confuses fecal occult blood originating in the upper GI with fetal occult blood originating in the lower intestine during those times the stool has a relatively long residency time in the bowel. The residual digestive enzymes in the stool and active bacteria in the stool rapidly digest blood originating from the lower GI tract, sometimes in as little as one hour in some individuals. This degradation causes the hemoglobin in the lower GI blood to be broken down and to resemble blood which originates in the upper GI tract in its migration pattern on chromatographic test paper. Administration of a laxative purge, however, not only dilutes the stool, but also buffers it thereby reducing the degradation of lower GI blood which allows it to retain its characteristic chromatographic migration pattern. Without being bound to any particular theory, it is believed that this retardation of hemoglobin degradation is achieved in part by the sequestering of divalent ions such as calcium because such ions are necessary both for bacterial growth and for many enzymatic reactions.

The example below illustrates this rapid loss of migratory capacity of whole blood (or hemoglobin) in solid stool samples and shows that the migratory capacity of hemoglobin is retained in watery stools obtained by the laxative purge, thus preserving the diagnostic sensitivity and specificity needed to separate upper GI from lower GI bleeding.

BASE LINE: MIGRATION OF HEMOGLOBIN vs. HEMATIN

Chromatography strips (approximately 3 x 0.5 centimeters) were prepared by affixing Whatman #1 filter paper to a polyvinyl backing. One microliter of sample was spotted at the origin and allowed to dry for one minute. One drop of solvent ( i.e., McIlvaine's buffer pH 5.0 ) was placed over the sample and was absorbed by the paper. When the solvent front was within 0.5 centimeters of the end of the strip, excess solvent was removed, and a layer of developing solution (i.e., o-Tolidine) was added. Results were recorded within one minute. Under these conditions, whole blood suspended in a solution containing ethylenediamine-tetraacetic acid (EDTA) (a preservative) migrates with an Rf of 0.5–1.0 while a solution of pure hematin has an Rf of 0 (i.e., it remains at the origin). Rf is the ratio of the sample migration distance to the solvent migration distance.

PREPARATION OF SOLID STOOL AND LIQUID STOOL BLOOD AND HEMATIN SAMPLES

Solid stool (SS) samples were prepared by mixing 1 gram solid stool with 100 microliters whole blood (hemoglobin) (SS-B) or 1 milligram pure hematin in solution (SS-H).

Liquid stools (LS) were obtained by oral administration of a purgative dose of Fleet's phosphosoda purge after a bowel movement as disclosed in the first embodiment. The first watery stool was collected and when 7 milliliters was added to 100 microliters whole blood (LS-B) or 1 milligram pure hematin in solution (LS-H).

EFFECT OF INCUBATION OF HEMOGLOBIN IN SOLID STOOL

As expected, SS-B and LS-B were positive for migration immediately after preparation while SS-H and LS-H were negative. Samples were then incubated at 37° C. to simulate physiologic conditions within the bowel lumen. Alternatively, they were left at room temperature or refrigerated for varying periods to assess sample stability.

The SS-B samples failed to migrate after 4 hours of refrigeration or one hour of 37° C. incubation. In addition, migration could not be selectively restored by heating (57° C. for 3 hours), treatment with detergents such as SDS, Triton X100 buffer, or NaCl solutions (1–5 Molar).

As shown in FIG. 1, LS-B samples, by contrast, retained their migratory properties for an incubation period of 22–27 hours at 37° C., two days at room temperature and more than five days upon refrigeration. Room temperature stability was extended to five days by adding 0.15% EDTA (final concentration). Though the sensitivity of this system was not optimized, similar results were seen at eight hours in LS samples containing 10 microliters of whole blood per seven milliliters of first watery stool. No migration was seen in LS-H of SS-H samples at any time regardless of temperature or EDTA concentration.

As noted above, LS-B samples were positive for migration immediately after preparation and for 27 hours when incubated at 37° C. in liquid form. However, it was discovered that if the LS-B samples were spotted on chromatography strips immediately after preparation and were left to dry, they lost their migrating capacity within 12 hours. Without wishing to be bound by any particular theory, it is speculated that this loss of migratory capacity was due to the hemoglobin binding to the paper after several hours of drying. Blood migration capacity was extended to approximately three days, however, if the strips were coated with silicone and 1% EDTA at the origin prior to spotting. No migration of LS-H samples was seen under these conditions.

DISCUSSION OF EXPERIMENTAL RESULTS

The above results demonstrate that the Wardlaw et al. test reliably distinguishes whole blood from hematin when using watery stool samples as compared to solid stool samples. Whole blood and hematin retained their differential properties when incubated under physioiogic conditions for approximately one day, a time period which far exceeds the duration of the laxative purge (6–12 hours) when colonic blood is in contact with the stool at 37° C. Thus, all bleeding occurring during the purge should be properly characterized with this system.

Another benefit is enhanced sample stability, which is an essential requirement for widespread utilization of fetal occult blood testing. Liquid stool samples containing whole blood or hematin are stable for up to five days with refrigeration or at room temperature with EDTA added as a preservative. In an alternative embodiment, when a HEMAWIPE format was utilized, spotted samples were stable for up to three days at room temperature on silicone-treated chromatography strips.

Of course, it is understood that the foregoing is a preferred embodiment of the invention and that various changes and alterations can be made without departing from the spirit and broader aspects thereof.

The embodiments of the invention in which an exclusive property or privilege is claimed are defined as follows.

1. A method for obtaining a stool sample to test for the presence of chemical markers associated with gastrointestinal cancer comprising:
    administering a laxative purge to a patient being tested for gastrointestinal cancer;
    collecting a watery stool sample from the patient after administering said laxative purge; and
    subjecting said collected watery stool sample to a diagnostic assay which tests for the presence of chemical markers associated with gastrointestinal cancer.

2. A method in accordance with claim 1 in which said collected watery stool sample is collected by voiding a first stool from the patient's bowel after said laxative purge, followed by collecting a second stool after said first stool.

3. A method in accordance with claim 1 in which said collected watery stool sample is collected by voiding a first stool from the patient's bowel prior to said administering step and collecting a first watery stool sample passed after said laxative purge, which thereby comprises said collected watery stool sample.

4. The method of claim 1 in which a first watery stool after administering said laxative purge is discarded and a second watery stool is collected, thereby comprising said collected watery stool sample, and subjected to said diagnostic assay which tests for the presence of chemical markers associated with gastrointestinal cancer.

5. The method of claim 1 which includes adding a preservative to said collected watery stool sample and storing said preservative and collected watery stool sample combination prior to said diagnostic assay which tests for the presence of chemical markers associated with gastrointestinal cancer.

6. A method in accordance with claim 5 in which said collected watery stool sample is collected by voiding a first stool from the patient's bowel after said laxative purge, followed by collecting a second stool after said first stool.

7. A method in accordance with claim 5 in which said collected watery stool sample is collected by voiding a first stool from the patient's bowel prior to said administering step and collecting a first watery stool sample passed after said laxative purge, which thereby comprises said collected watery stool sample.

8. The method of claim 5 in which a first watery stool after administering said laxative purge is discarded and a second watery stool is collected. thereby comprising said collected watery stool sample, and subjected to said diagnostic assay which tests for the presence of chemical markers associated with gastrointestinal cancer.

9. A method for obtaining a stool sample to test for the presence of fecal occult blood comprising:
    administering a laxative purge to a patient being tested for gastrointestinal cancer;
    collecting a watery stool sample from the patient after administering said laxative purge; and
    subjecting said collected watery stool sample to a fecal occult blood diagnostic assay.

10. A method in accordance with claim 9 in which said collected watery stool sample is collected by voiding a first stool from the patient's bowel after said laxative purge, followed by collecting a second stool after said first stool.

11. A method in accordance with claim 9 in which said collected watery stool sample is collected by voiding a first stool from the patient's bowel prior to said administering step and collecting a first watery stool sample passed after said laxative purge, which thereby comprises said collected watery stool sample.

12. The method of claim 9 in which a first watery stool after administering said laxative purge is discarded and a second watery stool is collected, thereby comprising said collected watery stool sample, and subjected to said fecal occult blood diagnostic assay.

13. The method of claim 9 which includes adding a preservative to said collected watery stool sample and storing said preservative and collected watery stool sample combination prior to said fecal occult blood diagnostic assay.

14. A method in accordance with claim 13 in which said collected watery stool sample is collected by voiding a first stool from the patient's bowel after said laxative purge, followed by collecting a second stool after said first stool.

15. A method in accordance with claim 13 in which said collected watery stool sample is collected by voiding a first stool from the patient's bowel prior to said administering step and collecting a first watery stool sample passed after said laxative purge, which thereby comprises said collected watery stool sample.

16. The method of claim 13 in which a first watery stool after administering said laxative purge is discarded and a second watery stool is collected, thereby comprising said collected watery stool sample, and subjected to said fecal occult blood diagnostic assay.

* * * * *

UNITED STATES PATENT AND TRADEMARK OFFICE
CERTIFICATE OF CORRECTION

PATENT NO. : 5,331,973
DATED : July 26, 1994
INVENTOR(S) : Paul N. Fiedler et al.

It is certified that error appears in the above-indentified patent and that said Letters Patent is hereby corrected as shown below:

Column 3, Line 9:

"titrate" should be --citrate--.

Column 4, Line 11:

"fetal" should be --fecal--.

Column 5, Line 62:

"fetal" should be --fecal--.

Signed and Sealed this

Twenty-eight Day of February, 1995

Attest:

BRUCE LEHMAN

*Attesting Officer*    *Commissioner of Patents and Trademarks*